United States Patent [19]

Tremulis

[11] Patent Number: 5,159,937
[45] Date of Patent: Nov. 3, 1992

[54] STEERABLE DILATATION CATHETER

[75] Inventor: William S. Tremulis, Redwood City, Calif.

[73] Assignee: Advanced Cardiovascular Systems, Inc., Santa Clara, Calif.

[21] Appl. No.: 624,207

[22] Filed: Dec. 7, 1990

Related U.S. Application Data

[60] Division of Ser. No. 528,860, May 25, 1990, Pat. No. 5,050,606, which is a continuation of Ser. No. 401,031, Aug. 31, 1989, Pat. No. 4,964,409, which is a continuation-in-part of Ser. No. 350,500, May 11, 1989, Pat. No. 4,953,553, which is a continuation-in-part of Ser. No. 103,109, Sep. 30, 1987, abandoned.

[51] Int. Cl.$^5$ ............................................... A61B 5/00
[52] U.S. Cl. ........................................ 128/772; 606/194; 604/164; 128/657
[58] Field of Search ............... 128/657, 772; 606/192, 606/193, 194; 604/95, 96, 164, 170, 280, 282, 264

[56] References Cited

U.S. PATENT DOCUMENTS

| | | | |
|---|---|---|---|
| 4,641.654 | 2/1987 | Samson et al. | 128/657 |
| 4,832,023 | 5/1989 | Murphy-Chutorian et al. | 606/7 |
| 4,917,088 | 4/1990 | Crittenden | 606/194 |
| 4,981,478 | 1/1991 | Evard et al. | 604/282 |

Primary Examiner—Randy C. Shay
Attorney, Agent, or Firm—Crosby, Heafey, Roach & May

[57] ABSTRACT

A guiding member for use as an independent guidewire or as an integral part of a low-profile steerable dilatation catheter. The guiding member has an elongated main hollow tubular member, a tubular extension preferably made of polyimide secured to the distal end of the tubular member, a core member which is secured by the proximal end thereof within the inner lumen of the main tubular member and which extends through and out of the distal end of the tubular extension and a flexible body, such as a helical coil, disposed about and secured to the distal portion of the core member which extends out the distal end of the tubular extension. The transverse cross-sectional area of the core member disposed within the inner lumen of the main tubular member should be at least 10%, preferably at least 25% less than the transverse cross-sectional area of the inner lumen of the main tubular member. The distal tip of the main tubular member is at least 15 cm, preferably between 25 and 60 cm proximal to the distal end of the coil to ensure that the transition region where the core member and the tubular extension join the main tubular member remains within the guiding catheter during vascular procedures therewith. When employed as part of a steerable catheter, the inflatable balloon is secured by the proximal end thereof to the distal end of the tubular extension and by the distal end of the core member which extends therethrough.

14 Claims, 2 Drawing Sheets

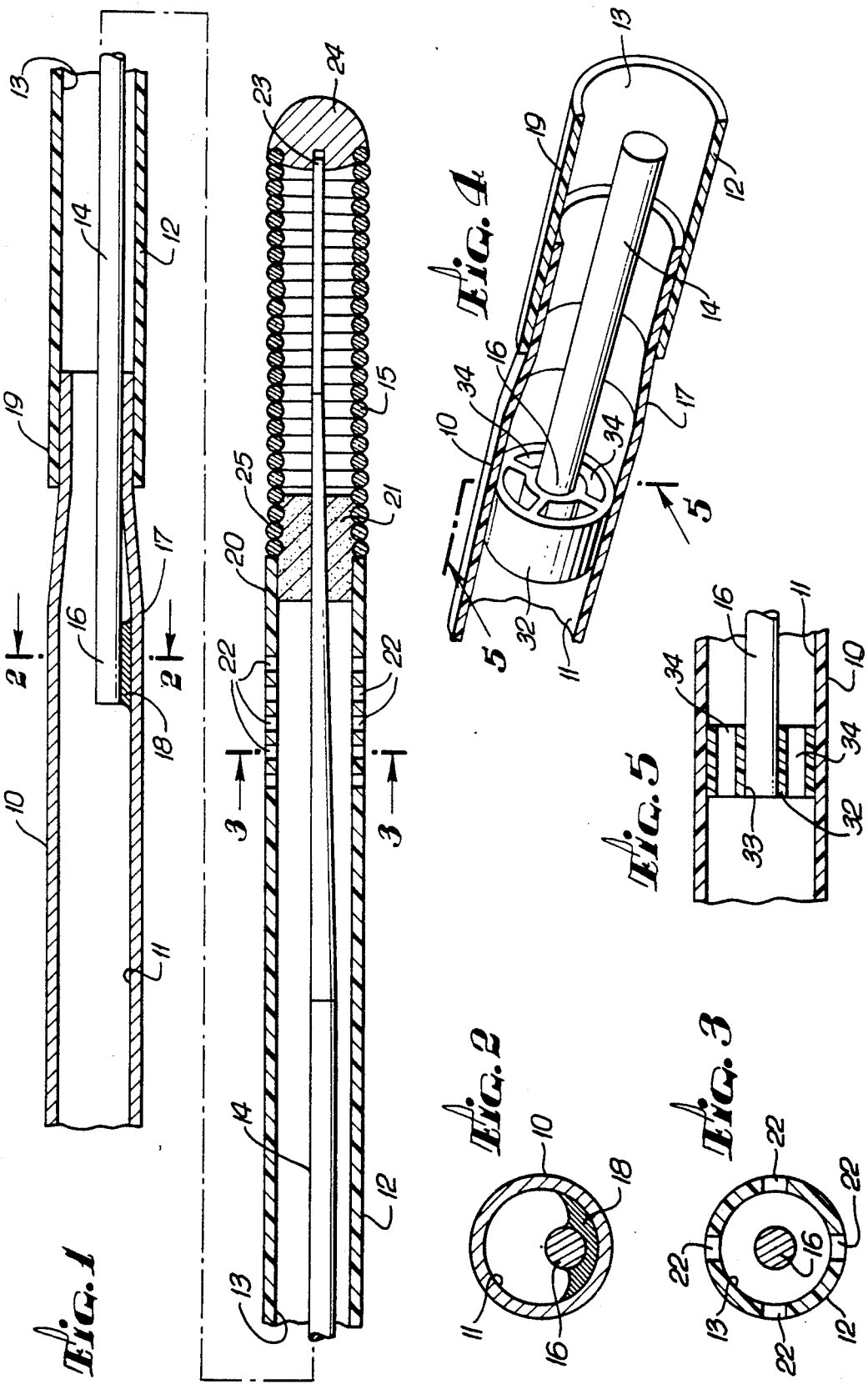

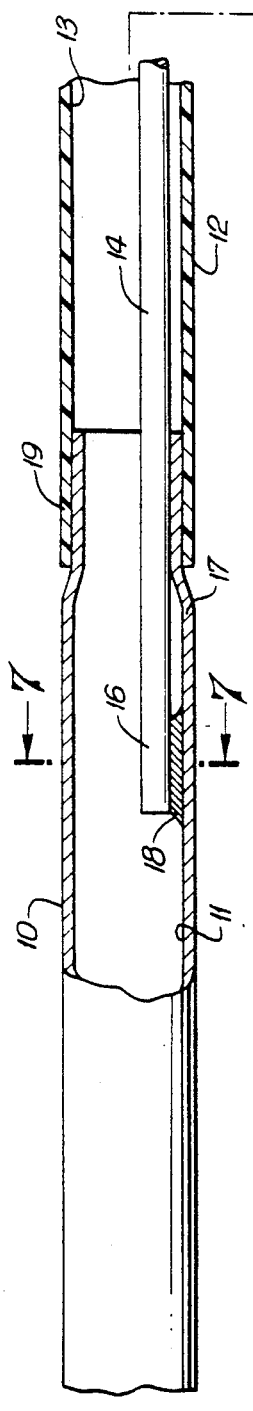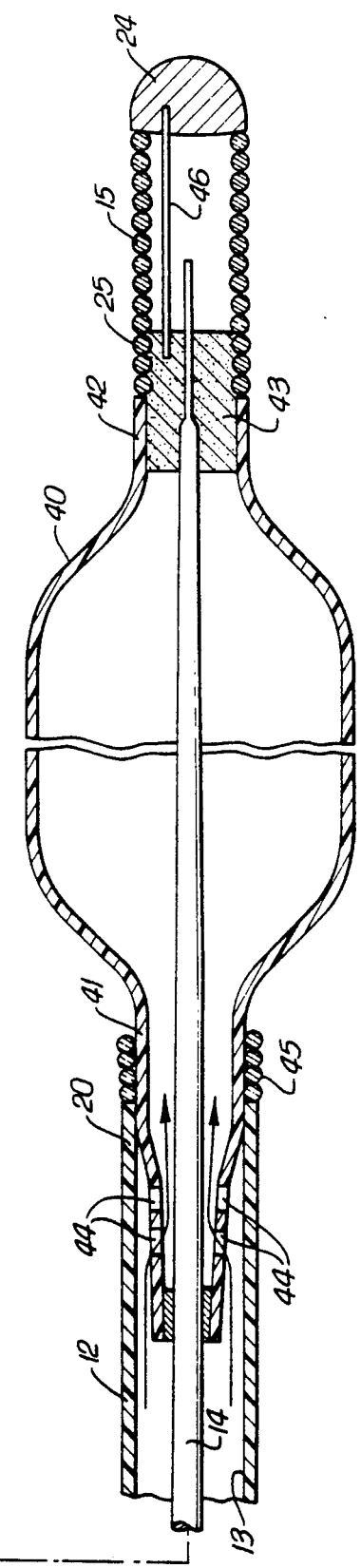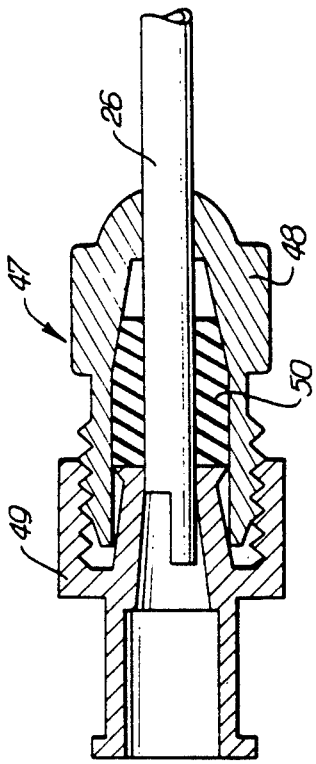

STEERABLE DILATATION CATHETER

This is a divisional of the application Ser. No. 07/528,860 which was filed on May 25, 1990, now U.S. Pat. No. 5,050,606 which was a continuation of the application Ser. No. 07/401,031 which was filed on Aug. 31, 1989, which is now U.S. Pat. No. 4,964,409, which was a continuation-in-part of application Ser. No. 350,500, filed May 11, 1989, now U.S. Pat. No. 4,953,553, which was a continuation-in-part of application Ser. No. 103,109, filed Sep. 30, 1987, now abandoned.

BACKGROUND OF THE INVENTION

This invention generally relates to guiding members for the advancement of catheters within a patient's vascular system in procedures such as percutaneous transluminal coronary angioplasty (PTCA) and particularly to such guiding members which facilitate the monitoring of pressure at the distal end thereof or the delivery of inflation fluid to a dilatation balloon.

In typical PTCA procedures a guiding catheter having a preformed distal tip is percutaneously introduced into the cardiovascular system of a patient and advanced therein until the distal tip thereof is in one of the patient's coronary arteries. A guidewire is introduced through the guiding catheter and advanced out of the distal end of the guiding catheter and into the patient's coronary vasculature until the distal end of the guidewire crosses a lesion to be dilated. A dilatation catheter having an inflatable balloon on the distal portion thereof is then advanced into the patient's coronary anatomy over the previously introduced guidewire, with the guidewire slidably disposed within an inner lumen of the dilatation catheter, until the dilatation balloon is properly positioned across the lesion. Once in position across the lesion, the balloon is inflated to a predetermined size with radiopaque liquid at relatively high pressures (e.g., greater than 4 atmospheres) to compress the atherosclerotic plaque of the lesion against the inside of the artery wall. The balloon is then deflated so that the dilatation catheter can be removed and blood flow resumed through the dilated artery.

Steerable dilatation catheters with built-in guiding members are being used with increasing frequency because the deflated profiles of such catheters are generally much smaller than conventional dilatation catheters and a smaller profile allows the catheter to cross tighter lesions and to be advanced much deeper into the patient's coronary anatomy. Additionally, the use of steerable low-profile dilatation catheters can shorten the time for the angioplasty procedures because there is no need to first advance a guidewire through the stenosis and then advance a conventional dilatation catheter over the previously placed guidewire.

Further details of dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson), U.S. Pat. No. 4,538,622 (Samson et al.); U.S. Pat. No. 4,582,181 (Samson); U.S. Pat. No. 4,616,652 (Simpson); U.S. Pat. No. 4,619,263 (Frisbie et al.) U.S. Pat. No. 4,638,805 (Powell); U.S. Pat. No. 4,641,654 (Samson et al.); U.S. Pat. No. 4,721,117 (Mar et al.); and U.S. Pat. No. 4,821,722 (Miller et al.) which are hereby incorporated herein in their entirety by reference thereto.

Efforts have been made, such as described in U.S. Pat. No. 4,582,181, to develop hollow guidewire systems which allow for the measurement of the fluid pressure at the distal end of the catheter from the proximal end of the catheter. However, usually such pressure sensing guidewires do not have the flexibility in the distal portion thereof to be advanced very far into a patient's vasculature, particularly the coronary arteries. What has been needed and heretofore unavailable is a guiding member which has sufficient flexibility in the distal portion thereof to be easily advanced through a patient's arteries and which can monitor from the proximal end thereof the fluid pressure within the patient's artery at the distal end of the guidewire. The present invention satisfies that need.

SUMMARY OF THE INVENTION

The present invention is directed to an improved flexible guiding member which can be utilized for monitoring of fluid pressure during intravascular procedures such angioplasty, angiography, and valvuloplasty, or which can be utilized to direct inflation fluid to the interior of a dilatation balloon during angioplasty or valvuloplasty procedures.

The guiding member in accordance with the invention includes a main elongated tubular member having an inner lumen extending therethrough to an axial port in the distal end thereof. A core member is secured by the proximal end thereof within the inner lumen of the main tubular member and extends out the distal end of the main tubular member. A tubular extension is disposed about the portion of the core member which extends out the distal end of the main tubular member and is secured by the proximal end thereof to the distal end of the main tubular member. A flexible body such as a helical coil is disposed about and secured to a portion of the core member which extends out the distal end of the tubular extension. The diametrical dimensions of the proximal portion of the core member disposed within the inner lumen of the main tubular member are substantially less than the smallest dimensions of the inner lumen, including the axial opening thereof, so as to not impede the flow of fluid therethrough or the passage therethrough of fluid pressure pulses. The transverse cross-sectional area of the core member should be at least 10% less than the smallest transverse cross section of the inner lumen of the main tubular member, preferably less than 25% of said cross-sectional area.

When the guiding member of the invention is utilized in an independent guidewire configuration, the distal end of the tubular extension is bonded to the core member extending therethrough and preferably immediately adjacent the proximal end of the helical coil to provide a relatively smooth transition. The distal end of the tubular extension is provided with one or more pressure monitoring ports which connect in fluid communication the inner lumen of the main tubular member with the ambient surrounding through the inner lumen in the tubular extension.

When the invention is utilized in a low-profile steerable dilatation catheter configuration, an inflatable balloon is secured by the proximal end thereof to the distal end of the tubular member so as to complete the structure of the outer catheter body. The distal end of the balloon is sealed about the portion of the core member which extends out the distal end thereof so as to prevent the loss of inflation fluid during angioplasty procedures. Means may be provided to vent air from the interior of the balloon, such as described in U.S. Pat. No. 4,638,805 (Powell) and U.S. Pat. No. 4,821,722 (Miller et al.).

Due to the relatively large difference in cross section between the inner lumen of the tubular member and the outer diameter of the proximal end of the core member which is secured within the inner lumen of the tubular member, the transition between the distal end of the main tubular member, the proximal end of the core member and the proximal end of the tubular extension does not significantly interfere with either the passage of fluid as when inflating a dilatation balloon on the distal end thereof or the passage of pressure pulses when taking pressure measurements from the proximal end of the tubular member. The transition region of the vascular device may be relatively stiff, but the effects of the relatively stiff transition can be minimized by disposing the transition region sufficiently proximal from the distal end of the guiding member to ensure that it remains within the guiding catheter during vascular procedures and that only the flexible portion of the vascular device are advanced into the patient's tortuous coronary anatomy. Typically, the transition region should be at least 25 cm, preferably at least 40 cm, from the distal tip of the guiding member. However, generally it should not exceed about 60 cm from the distal tip of the guiding member so as to not reduce the pushability of the distal portion of the catheter body.

The tubular extension is diametrically relatively rigid to prevent kinking, but it is longitudinally more flexible than the main tubular member because it is this distal portion of the guiding member which must be advanced out of the guiding catheter into the patient's tortuous coronary vasculature.

The distal portion of the guiding member in accordance with the invention readily advances through a patient's vasculature and particularly through the coronary anatomy thereof. Moreover, it provides for effective pressure monitoring from the proximal end thereof as a guidewire and it allows for the rapid inflation and deflation of a dilatation balloon on the distal portion thereof when the guiding member is fixed within a steerable catheter. These and other advantages of the invention will become more apparent from the following detailed description thereof when taken in conjunction with the accompanying exemplary drawings.

BRIEF DESCRIPTION OF THE DRAWINGS

FIG. 1 is a fragmentary centerline sectional view of a guiding member embodying features of the invention;

FIG. 2 is a transverse sectional view taken along the lines 2—2 shown in FIG. 1;

FIG. 3 is a transverse sectional view taken along the lines 3—3 shown in FIG. 1;

FIG. 4 is a perspective view in section of an alternative embodiment of the invention;

FIG. 5 is a longitudinal view in section taken along the lines 5—5 shown in FIG. 4;

FIG. 6 is a fragmentary centerline sectional view of a guiding member with features of the invention embodied as a low-profile dilatation catheter;

FIG. 7 is a transverse sectional view taken along the lines 7—7 shown in FIG. 6; and, FIG. 8 is a centerline cross-sectional view of a Touhy-Borst adapter which is mounted onto the proximal end of the guiding member shown in FIGS. 6 and 7.

DETAILED DESCRIPTION OF THE INVENTION

FIGS. 1-3 illustrate a guiding member embodying features of the invention which generally include a main tubular member 10 having an inner lumen 11, a longitudinally flexible tubular extension 12 having an inner lumen 13, a core member 14 and a helical coil 15 disposed about the distal extremity of the core member. The main tubular member 10 is preferably provided with an outer coating of a lubricious material (not shown), such as Teflon. The proximal end 16 of the core member 14 is secured within the distal end 17 of the main tubular member 10 by means of a weldment 18 and has a transverse cross-sectional area substantially less than the smallest transverse cross-sectional area of the inner lumen 11 of the main tubular member 10.

The tubular extension 12 is secured at its proximal end 19 to the distal end 17 of the main tubular member 10 and at its distal end 20 to core member 14 by suitable means such as adhesive 21. A plurality of pressure monitoring ports 22 are provided in the distal portion thereof to connect in fluid communication the inner lumen 11 of the main tubular member 10 with the ambient through the inner lumen 13 of the tubular extension 12. The distal end 23 of core member 14 is secured to the rounded plug 24, preferably made of radiopaque material, at the distal end of the coil 15. The proximal end 25 of coil 15 is bonded by adhesive 21 to the core member 14. The vascular device of the invention can alternatively have a "floppy" structure as shown in FIG. 6 and in U.S. Pat. No. 4,554,929 (Samson et al.), and U.S. Pat. No. 4,538,622 (Samson et al.), wherein the core member 14 terminates short of the distal end of the coil 15 and a shaping ribbon 46 (not shown in FIG. 1) secured to the core member extends to the rounded plug 24.

The elongated main tubular member 10 is preferably made of stainless steel or a superelastic nickel-titanium alloy and is in the form of hypotubing. The core 14 is preferably a solid member formed of stainless steel. The helical coil 15 is preferably formed from a wire of palladium-platinum-molybdenum alloy or platinum-nickel alloy which has been gold plated. The tubular extension 12 is preferably formed from a polyimide, such as described in copending application Ser. No. 302,584, filed Jan. 26, 1989, which is hereby incorporated herein by reference.

Suitable dimensions of the various members of the guidewire shown in FIGS. 1-3 for coronary applications are given as follows with typical dimensions being provided in parentheses. The main tubular shaft 10 is generally about 120 to about 160 cm (140 cm) in length with an outer diameter of about 0.012 to about 0.018 inch (0.015 inch) and an inner diameter of about 0.007 to about 0.013 inch (0.01 inch). The tubular extension 12 is about 25 to about 45 cm (33 cm) in length with the outer diameter thereof from about 0.0065 to about 0.0125 inch (0.0095 inch) and the inner diameter from about 0.0035 to about 0.0085 inch (0.006 inch). The core member 14 ranges from about 25 to about 45 cm (35 cm) in length with the tapered section thereof being about 2 to about 6 cm (2.5 cm) in length. The outer diameter of the main portion of the core member 14 is about 0.004 to about 0.012 inch (0.0065 inch) with the smallest size of the tapered section being rectangular in shape and about 0.0015 to about 0.004 inch. The wire forming coil 15 is about 0.002 to about 0.003 inch (0.0025, inch) in diameter and the coil section is about 1.5 to about 5 cm in length (3 cm) and has an outer diameter of about 0.01 to about 0.15 inch (0.0125 inch). The pressure monitoring ports 22 in the tubular extension 12 generally number about 10 to 40 (20) and they are generally about 0.0015 to about 0.0045 inch (0.002 inch) in diameter. Preferably, these ports are equally spaced in linearly arranged groups about the periphery of the member in which they are formed. The guidewire of the invention which is suitable for angioplasty will have an outer diameter from about 0.01 to about 0.038 inch, whereas for valvuloplasty the outer diameter will range from about 0.025 to about 0.045 inch.

FIGS. 4 and 5 illustrate an alternative method of joining the proximal end 16 of the core member 14 within the distal end 17 of the main tubular member 10 wherein a cylindrically shaped support element 3 is secured within the distal end 17 of the tubular member. The proximal end 16 of the core member 14 is fixed within the central passageway 33 of the support element 32. Fluid flow passageways 34 are provided about the central passageway 33 to allow for fluid communication between the inner lumen 11 of the main tubular member 10 and the inner lumen 13 of the tubular extension 12. The cylindrically shaped supporting element 32 may be made of suitable material, including plastic or metals and is fixed within the inner lumen 11 of the main tubular member 10 by suitable means such as adhesive.

In the vascular device of the present invention, metal-to-metal bonding may be effected by welding, soldering, brazing and the like, whereas bonding to plastic materials may be effected by means of a suitable adhesive, such as a cyanoacrylate (Loktite 405).

In a typical operation of a guidewire in accordance with the present invention, the guidewire is introduced into an inner lumen of a dilatation catheter and then both are advanced through a guiding catheter previously disposed within a patient's vasculature with the distal end of the guiding catheter positioned within the ostium or opening of the patient's desired coronary artery. The guidewire of the invention is then advanced out of the distal tip of the guiding catheter into the patient's coronary artery with the pressure monitoring ports 22 in a desired location, e.g., distal to the stenosis, so that pressure measurements may be taken prior to angioplasty procedures. The dilatation catheter may then be advanced over the guidewire until the balloon thereof crosses the stenosis where it is inflated and deflated in a normal manner to perform the dilatation. After deflating of the balloon, the guidewire of the invention is still in position with the pressure ports thereof distal to the stenosis so that further pressure monitoring may be made to determine the effectiveness of the angioplasty procedure.

The guidewire of the invention has extensive applications in cardiovascular procedures, such as angioplasty, angiography, and valvuloplasty. A pressure gradient can be measured between the guiding catheter at the coronary ostium and the distal tip of the guidewire on the distal side of the lesion before and after the dilation of the stenotic lining. The present guidewire design eliminates the need for any pressure monitorings through the lumen of the dilatation catheter which permits the dilatation catheter to be constructed with a much lower profile than conventional dilatation catheters, thus making it possible to monitor distal pressures through catheters of very low profile. Accurate pressure readings can be obtained regardless of whether the balloon on the dilatation catheter is inflated or deflated.

When the balloon is inflated, pressure determinations for the coronary anatomy distal to the inflated balloon can identify the presence of collateral circulation distal to the lesion and can identify other circulatory anomalies. The guidewire is highly torquable and is readily steered to facilitate placement deep within the patient's coronary vascular system. Moreover, there is little tendency for the distal portion of the guidewire, i.e., the most distal 20 to 60 cm's thereof, to develop a permanent curved set when passing through the curved distal tip of the guiding catheter, even through the tip can have a radius of curvature as small as 0.5 cm.

FIGS. 6-8 illustrate an embodiment of the invention in the form of a low-profile steerable dilatation catheter. This embodiment is very similar to that shown in FIGS. 1-3 and therefore similar parts are numbered the same. Included is main elongated tubular member 10 within an inner lumen 11, a tubular extension 12 secured by the proximal end 19 thereof to the distal end 17 of the tubular member 10, a core member 14 secured by the proximal end thereof within the distal end 17 of the tubular member 10, and an inflatable balloon member 40 which is bonded by the proximal end 41 and distal end 42 thereof to the core member 14.

The core member 14 is fixed to the inner wall of the main tubular member 10 and extends distally therefrom through the inner lumens 11 and 13 and interior of the balloon member 40 and out the distal end thereof. A helical coil 15 is disposed about the portion of core member 14 which extends out the distal end 42 of the balloon and is secured at location 43 and the plug 24. The proximal end or skirt 41 and the distal end or skirt 42 of the balloon member 40 are both bonded directly or indirectly to the core member 14 by suitable means in order to prevent the wrapping of the balloon when the catheter is steered through a patient's artery to the site of the stenosis.

The proximal end 41 of the balloon 40, while bonded by suitable adhesive to the core member 14, is radially spaced therefrom so that inflation fluid can pass through inlet ports 44 provided in the proximal skirt 41 into the interior of the balloon 40 to inflate same during angioplasty procedures. A radiopaque marker coil 45 is provided at the adhesive joint between the distal end 20 of the tubular extension 12 and the balloon 40.

The helical coil 15 shown in FIG. 5 has a floppy construction wherein the longitudinal extension of the core member 14 terminates short of the rounded plug 24 and a shaping ribbon 46 which is secured to the core member 14 extends and is secured to the radiopaque rounded plug.

As shown in FIG. 8, the proximal end 26 of tubular member 10 is provided with a Touhy-Borst adapter 47 to allow the tubular member to be rotated and to direct inflation fluid into the inner lumen 11 thereof. The adapter 47 is of conventional construction with a housing 48 and a cap 49 threadably connected to the housing and an annular sealing member 50 disposed about the proximal end 26 of the main tubular member 10. The inner cavity within the housing 48 is tapered so that the tightening of the cap 49 will force the sealing member 50 against the outside of the proximal end 26 of the main tubular member 10 thereby effecting a fluid-tight seal.

The materials of construction which are suitable for this embodiment generally are those which are suitable for the previously discussed embodiment. The shaping ribbon may be stainless steel but is preferably a gold plated tungsten-rhenium alloy. The balloon is preferably made of a biaxially oriented polymer such as polyethylene or polyethylene terephthalate. In the latter instance, the polymer is preferably formed from a thermoplastic resin having an intrinsic viscosity of about 0.75 to 1.25, preferably less than 1.0. The wall thickness of the balloon in the cylindrical or working section ranges from about 0.0002 to about 0.0005 inch, whereas in the proximal and distal ends thereof the thickness ranges from about 0.0008 to about 0.002 inch.

Typical dimensions of the steerable, low-profile dilatation catheter of the invention include an overall length of approximately 150 to about 200 cm, a tip coil length from about 1 to 3 cm, a balloon length of about 1 to 3 cm, and inflated balloon diameters from about 1 to about 5 mm. Deflated profiles for the balloon range from about 0.01 to about 0.025 inch (0.254 mm–0.635 mm) preferably less than about 0.02 inch (0.508 mm).

The low-profile steerable dilatation catheter of the invention can be used in the same manner as prior low-profile steerable dilatation catheters. However, because of the smaller profiles available with the dilatation catheters of the present invention, much tighter stenoses can be crossed than with prior devices. Moreover, the dilatation catheter of the invention can be readily advanced through very tortuous arterial passageways with little risk of wrapping the balloon on itself thus ensuring complete inflation and deflation when it is positioned within a stenosis to be dilated. Additionally, the dilatation catheter with a preferred profile of less than 0.02 inch can be used as described in copending application Ser. No. 760,636, (which is hereby incorporated herein by reference) to be advanced through the inner lumen of a standard dilatation catheter in order to first dilate a stenosis with the smaller dilatation catheter so that the larger profile standard dilatation catheter can then be advanced into the predilated stenosis to complete the dilatation. The Touhy-Borst adapter on the proximal end of the main tubular member in accordance with the invention provides the further advantage in that it can be removed, an exchange wire inserted into the proximal end of the main tubular member and the standard dilatation catheter can be exchanged with another standard dilatation catheter over the low-profile steerable catheter of the invention. Other uses of the invention will become apparent to those skilled in the art.

While the above description of the invention is directed to presently preferred embodiments, various modifications and improvements can be made without departing from the scope of the invention.

What is claimed is:

1. A steerable dilatation catheter for angioplasty procedures, comprising:
   a) a main tubular member having proximal and distal ends and an inner lumen extending therethrough to an axial opening in the distal end thereof;
   b) a tubular extension having an inner lumen and being secured by the proximal end thereof to the main tubular member;
   c) a solid elongated core member which has a proximal end secured within the inner lumen of the main tubular member, which extends out the axial opening in the distal end of the main tubular member, through the inner lumen of the tubular extension and out of the distal end of the tubular extension and which has a section extending through the axial opening with a transverse cross-sectional area substantially less than the cross-sectional area of the opening to facilitate the passage of inflation fluid therethrough;
   d) an inflatable balloon having a proximal end and a distal end, with the proximal end secured to the distal end of the tubular extension and the distal end of the balloon secured to the core member passing therethrough; and
   e) a flexible body disposed about a portion of the core member which extends out the distal end of the inflatable balloon.

2. The steerable dilatation catheter of claim 1 wherein the flexible body is a helical coil.

3. The steerable dilatation catheter of claim 2 wherein the helical coil is formed of an alloy selected from the group consisting of platinum-palladium-molybdenum and platinum-nickel and is gold plated.

4. The steerable dilatation catheter of claim 1 wherein the core member and tubular extension are secured to the main tubular member in a transition region which is located at least 15 cm proximal to the distal tip of the flexible body to ensure that the transition region remains within the guiding catheter during angioplasty procedures.

5. The steerable dilatation catheter of claim 4 wherein the transition region is about 25 to about 60 cm proximal to the distal tip of the flexible body.

6. The steerable dilatation catheter of claim 1 wherein the tubular extension is formed of polyimide.

7. The steerable dilatation catheter of claim 1 wherein the main tubular member is formed of a metal selected from the group consisting of stainless steel and a superelastic alloy of nickel and titanium.

8. The steerable dilatation catheter of claim 1 wherein the proximal end of the core member is bonded to an inner wall of the main tubular member which defines the inner lumen thereof.

9. The steerable dilatation catheter of claim 8 wherein the core member is bonded to the inner wall by welding.

10. The steerable dilatation catheter of claim 1 wherein the transverse cross-sectional area of the core member within the inner lumen of the main tubular member is at least 25% less than the transverse cross-sectional area of the main tubular member in the section thereof wherein the core member is disposed.

11. The steerable dilatation catheter of claim 1 wherein a cylindrically shaped supporting element having at least one recess or passageway is fixed within the inner lumen of the main tubular member and the proximal end of the core member is fixed within said recess or passageway.

12. The steerable dilatation catheter of claim 11 wherein the recess or passageway within which is fixed the proximal end of the core member is centrally disposed within the supporting element.

13. The steerable dilatation catheter of claim 11 wherein the cylindrically shaped supporting element is provided with a plurality of fluid flow passageways therethrough and the transverse cross-sectional area of the core member is at least 10% less than the total transverse cross-sectional area of the fluid flow passageways.

14. The steerable dilatation catheter of claim 13 wherein the transverse cross-sectional area of the core member disposed within the main tubular member is at least 25% less than the total transverse cross-sectional area of the fluid flow passageways therein.

* * * * *